| United States Patent [19] | | [11] | 4,241,217 |
|---|---|---|---|
| Kuczkowski | | [45] | Dec. 23, 1980 |

[54] ANTIOXIDANT COMBINATION OF ESTERS AND AMINES

[75] Inventor: Joseph A. Kuczkowski, Cuyahoga Falls, Ohio

[73] Assignee: The Goodyear Tire & Rubber Company, Akron, Ohio

[21] Appl. No.: 909,746

[22] Filed: May 26, 1978

Related U.S. Application Data

[62] Division of Ser. No. 668,567, Mar. 19, 1976, Pat. No. 4,125,515.

[51] Int. Cl.$^3$ .......................................... C07C 149/20
[52] U.S. Cl. .................................... 560/152; 560/15; 560/17; 560/139; 560/144; 560/145
[58] Field of Search ........................................ 560/152

[56] References Cited

U.S. PATENT DOCUMENTS

| 2,601,063 | 6/1952 | Smith, Jr. et al. | 560/152 |
|---|---|---|---|
| 2,603,654 | 7/1952 | Kosmin | 560/152 |
| 3,244,683 | 4/1966 | Kline | 526/238 |
| 3,305,584 | 2/1967 | Spacht | 260/576 |
| 3,629,194 | 12/1971 | Onishi et al. | 260/45.95 R |
| 3,658,769 | 4/1972 | Kline | 260/78 |
| 3,739,026 | 6/1973 | Wilson | 260/576 |
| 3,758,549 | 9/1973 | Dexter et al. | 560/152 |
| 3,781,361 | 12/1973 | Wheeler | 260/45.9 QB |

*Primary Examiner*—Vivian Garner
*Attorney, Agent, or Firm*—J. Y. Clowney

[57] ABSTRACT

Ester such as 3,6,9-trioxaundecane-1,11-bis (3-n-dodecylthiopropionate) when combined with conventional free amine antioxidants such as N,N'-diphenyl-paraphenylenediamine or with polymer bound antioxidants such as N-(4-anilinophenyl) methacrylamide produce improved antioxidant systems for SBR and NBR type polymers.

1 Claim, No Drawings

ANTIOXIDANT COMBINATION OF ESTERS AND AMINES

This is a division of application Ser. No. 668,567 filed Mar. 19, 1976, now U.S. Pat. No. 4,125,515.

This invention relates to antioxidant systems. More particularly it relates to butadiene/styrene (SBR) and butadiene/acrylonitrile (NBR) polymers stabilized with two component antioxidant systems.

Those skilled in the art are constantly searching for new and more effective antioxidant systems which are useful for the protection of polymers. The need for such improved systems is the result of using polymers under more demanding and rigorous conditions. In particular, the use of polymers in automotive applications and the like, for example, as gaskets, has subjected polymers to high temperatures for great periods of time, thereby requiring long-lasting and persistent protection.

It is an object of the present invention to provide such long-lasting and persistent antioxidant systems. It is another object of the present invention to provide SBR and NBR polymer compositions which are well stabilized against oxidative degradation. Other objects will become apparent as the description proceeds.

The objects of the present invention are accomplished by the stabilization of SBR and NBR polymers with at least one amine antioxidant and at least one ester.

The ester has the following structural formula:

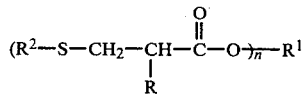

wherein n is an integer from 1 to 4, wherein R is selected from the group consisting of hydrogen and methyl, wherein when n is 1, $R^1$ is selected from the group consisting of alkyl radicals having 1 to 18 carbon atoms, aryl radicals having 6 to 12 carbon atoms, aralkyl radicals having 7 to 12 carbon atoms and cycloalkyl radicals having 5 to 12 carbon atoms wherein when n is 2, $R^1$ is selected from the group consisting of alkylene radicals having 2 to 18 carbon atoms, cycloalkylene radicals having 5 to 12 carbon atoms, arylene radicals having 6 to 12 carbon atoms,

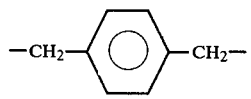

polyalkyl glycol ether radicals having the following structure

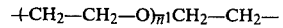

wherein $n^1$ is an integer from 1 to 7, a thioether radical having the following structure

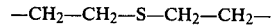

wherein when n is 3 or 4, $R^1$ is an aliphatic hydrocarbon radical having the formula $C_yH_{2y+2-n}$, wherein y is an integer from 3 to 6 and wherein $R^2$ is selected from the group consisting of alkyl radicals having 1 to 24 carbon atoms, (preferably primary alkyl), aryl radicals having 6 to 12 carbon atoms and aralkyl radicals having 7 to 12 carbon atoms.

The amine antioxidants are selected from the group consisting of N,N'-di-substituted-p-phenylenediamines, substituted diphenylamines, and both polymerized and non-polymerized derivatives of 2,2,4-trimethyl-1,2-dihydroquinoline (U.S. Pat. No. 3,244,683) as well as the amide and imide age resisters described in U.S. Pat. No. 3,658,769. The N,N'-di-substituted-p-phenylenediamines have the following structural formula:

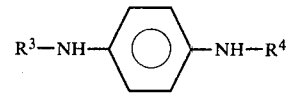

wherein $R^3$ and $R^4$ are selected from the group consisting of alkyl radicals having 3 to 12 carbon atoms, aryl radicals having 6 to 12 carbon atoms and aralkyl radicals having 7 to 12 carbon atoms and the diphenyl amines:

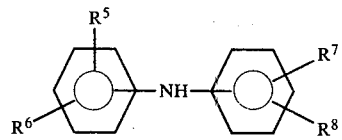

wherein $R^5$, $R^6$, $R^7$ and $R^8$ are selected from the group consisting of hydrogen, alkyl radicals having 1 to 20 carbon atoms and aralkyl radicals having 7 to 12 carbon atoms.

The teachings of U.S. Pat. No. 3,658,769 particularly as they relate to the description of the imide and amide compounds and their use in the preparation of SBR and NBR type polymers are incorporated herein by reference.

The compounds of U.S. Pat. No. 3,658,769 may be used within the practice of the present invention in free form such as described at column 6 of said reference, lines 62-67, or by polymerization techniques wherein they are chemically made part of the polymer as described throughout said reference, for example, at column 4, lines 58-62. The best synergistic results within the practice of the present invention are obtained when these compounds are polymerized into the polymer.

Compounds illustrating the above amines but not acting as limitations thereof are as follows:
N,N'-diphenyl-p-phenylenediamine
N,N'-di-beta-naphthyl-p-phenylenediamine
N-o-tolyl-N'-phenyl-p-phenylenediamine
N,N'-di-p-tolyl-p-phenylenediamine
N-1,3-dimethylbutyl-N'-phenyl-p-phenylenediamine
N-1,4-dimethylpentyl-N'-phenyl-p-phenylenediamine
N-isopropyl-N'-phenyl-p-phenylenediamine
N-1-methylpropyl-N'-phenyl-p-phenylenediamine
N-cyclohexyl-N'-phenyl-p-phenylenediamine
N,N'-bis-(1-ethyl-3-methylpentyl)-p-phenylenediamine
N,N'-bis-(1,4-dimethylpentyl)-p-phenylenediamine
N,N'-bis-(1-methylpropyl)-p-phenylenediamine
4,4'-bis-(di-alpha-methylbenzyl)-diphenylamine
4,4'-dioctyldiphenylamine
4,4'-dinonyldiphenylamine
polymerized-2,2,4-trimethyl-1,2-dihydroquinoline
6-dodecyl-1,2-dihydro-2,2,4-trimethylquinoline
6-ethoxy-1,2-dihydro-2,2,4-trimethylquinoline N-(4-anilinophenyl)methacrylamide as well as the compounds listed in column 3 of U.S. Pat. No. 3,658,769.

The amine compounds are well known in the art being described along with methods of preparation in U.S. Pat. Nos. 3,244,683; 3,658,769; 3,305,584; 3,739,026; 3,781,361; 3,452,056.

The esters of the present invention are illustrated by the following compounds.

*3,6,9-trioxaundecane-1,11-bis(3-n-dodecylthiopropionate)
*3,6-dioxaoctane-1,8-bis(3-n-dodecylthiopropionate)
3,6,9-trioxaundecane-1,11-bis(3-n-dodecylthio-2-methylpropionate)
3-oxapentane-1,5-bis(3-n-dodecylthiopropionate)

The asterisk (*) compounds are preferred compounds.

Other esters illustrating the esters of the present invention are as follows.
phenyl-(3-phenylthiopropionate)
phenyl-1,4-bis(3-t-dodecylthiopropionate)
naphthyl-1-(3-n-dodecylthiopropionate)
naphthyl-2-(3-n-octyl-2-methylpropionate)
naphthyl-1,4-bis(3-n-hexylthiopropionate)
phenyl-(3-n-dodecylthio-2-methylpropionate)
benzyl-(3-t-dodecylthiopropionate)
benzyl-(3-n-dodecylthio-2-methylpropionate)
p-xylyl-alpha,alpha'-bis(3-n-octyl-2-methylpropionate)
o-xylyl-alpha,alpha'-bis(3-n-dodecylthiopropionate)
ethane-1,2-bis(3-n-dodecylthiopropionate)
ethane-1,2-bis(3-t-dodecylthiopropionate)
butane-1,4-bis(3-benzylthiopropionate)
pentane-1,5-bis(3-n-hexylthio-2-methylpropionate)
propane-1,2-bis(3-n-dodecylthiopropionate)
octane-1,8-bis(3-n-tetracosylthiopropionate) 3,6,9-trioxaundecane-1,11-bis(3-phenylthiopropionate)
3,6,9-trioxaundecane-1,11-bis(3-benzylthio-2-methylpropionate)
3-oxapentane-1,5-bis(3-benzylthio-2-methylpropionate)
3-thiapentane-1,5-bis(n-octylthio-2-methylpropionate)
3-thiapentane-1,5-bis(benzylthio-2-methylpropionate)
1,1,1-trimethanolpropane-tris(3-n-octylthiopropionate)
1,1,1-trimethanolpropane-bis(3-t-dodecylthiopropionate)
pentaerythritol-tetrakis(3-phenylthiopropionate)
pentaerythritol-tetrakis(3-n-dodecylthio-2-methylpropionate)

The esters are also illustrated in U.S. Pat. Nos. 3,629,194 and 3,758,549, the contents of which particularly as they relate to the description of the esters and their preparation, are incorporated herein by reference.

The esters of the present invention can be prepared by reacting a suitable thiol with an ester of acrylic or methacrylic acid in the presence of a basic catalyst such as KOH or benzyl trimethyl ammonium hydroxide. In the case of aromatic hydroxy compounds such a process is preferred. The esters of the present invention may also be conveniently prepared by reacting a suitable acid with an alcohol in a known simple acid catalyzed esterification procedure as described in U.S. Pat. No. 2,601,063.

An alternate preparation of the esters involves the initial reaction of a suitable thiol with a lower alkyl ester of acrylic or methacrylic acid. The alkylthiopropionate ester is then transesterified with a high molecular weight glycol.

None of the compounds of the present invention are limited to the method of their preparation.

The SBR polymers which benefit by the practice of the present invention are those rubbery copolymers of butadiene/styrene in which the bound butadiene content is at least 50 percent by weight.

The NBR polymers which benefit by the practice of the present invention are those rubbery copolymers of butadiene and acrylonitrile in which the bound butadiene content is at least 55 percent by weight.

As noted earlier herein, the amide and imide compounds of U.S. Pat. No. 3,658,769 when used in the practice of the present invention may be chemically as opposed to physically incorporated into the SBR and NBR polymers by adding them to the monomer systems, i.e., butadiene and styrene or butadiene and acrylonitrile monomers prior to polymerization. Such techniques are described in U.S. Pat. No. 3,658,769.

The level of amine compound is from 0.25 to 5.0 parts by weight per 100 parts by weight of polymer. Preferably, the amine level is from 0.5 to 2.0 parts by weight. The weight of ester is from 1.0 to 20 parts by weight.

The sulfur vulcanized, both compounded and uncompounded versions of the SBR and NBR polymers, will benefit by the use of the antioxidant combination. Vulcanizing agents include free sulfur or compounds which are sulfur donors such as 2-(morpholinodithio) benzothiazole. The rubbers can be compounded with any conventional compounding ingredients such as carbon blacks, silica, zinc oxide, etc. The polymers are particularly benefited when exposed to high temperature, heat-aged type conditions. Vulcanization systems of both high and low efficiency benefit by the practice of the present invention.

The following examples are intended to illustrate but not to limit the practice of the present invention. Unless indicated otherwise, all parts are parts by weight per 100 parts by weight of rubber.

TABLE I

| Ingredients | Parts |
|---|---|
| NBR[(1)] | 100 |
| Stearic acid | 1 |
| Zinc oxide | 5 |
| Magnesium oxide | 5 |
| Silica | 50 |
| Coupling agent | .05 |
| Polyethylene glycols | 2 |
| Sulfur | .3 |
| 2-(morpholinodithio)-benzothiazole | 2.5 |
| 2-(morpholinothio)-benzothiazole | 1.3 |
| Zinc dimethyldithiocarbamate | 0.6 |

[(1)]67/33/1.6
1,3-butadiene/acrylonitrile
N-(4-anilinophenyl)
methacrylamide

The above formulation was compounded with various esters vulcanized and aged. The esters were used at the 2.5 part level. Tensile and elongation were measured on these vulcanizates as well as on a vulcanizate of the above formulation absent an ester, both before and after aging. The percent tensile and elongation retained after aging was calculated along with the percent tensile retained times percent elongation retained product. The higher these values, the better is the resistance of the polymer to aging.

The esters will be identified A,B,C, and D as follows:
A. 3,6-dioxaoctane-1,8-bis(3-n-dodecylthio-2-methylpropionate)
B. ethane-1,2-bis(3-n-dodecylthio-2-methylpropionate)
C. hexane-1,6-bis(3-n-dodecylthiopropionate)
D. 3,6,9-trioxaundecane-1,11-bis(3-n-dodecylthiopropionate)

TABLE II

| | Air Oven Aged at 300° F. % Retained | | | | | |
|---|---|---|---|---|---|---|
| | Tensile | | Elongation | | Tensile × Elongation | |
| Ester | 70 hr | 120 hr | 70 hr | 120 hr | 70 hr | 120 hr |
| — | 64 | 38 | 60 | 20 | 3840 | 760 |
| A | 72 | 52 | 68 | 26 | 4896 | 1352 |
| B | 77 | 42 | 62 | 20 | 4774 | 840 |
| C | 75 | 60 | 73 | 32 | 5475 | 1920 |
| D | 75 | 57 | 76 | 33 | 5700 | 1881 |

In each case the tensile x elongation product was superior to the control containing no ester.

In Tables III and IV are listed data on vulcanizates where the esters were added to an NBR latex prior to compounding.

Table III

| | Air Oven Aged 70 Hours at 300° F. % Retained | | |
|---|---|---|---|
| Ester | Tensile | Elongation | TXE |
| — | 64 | 34 | 2176 |
| A | 69 | 35 | 2415 |
| B | 67 | 32 | 2144 |
| C | 69 | 37 | 2553 |
| D | 68 | 37 | 2516 |

All but B possessed super TXE products. The rubber compositions were also aged in ASTM oil #3 for 70 hours at 300° F. followed by aging for 70 hours in an air oven at 300° F. The results are listed in Table IV.

Table IV

| | % Retained | | |
|---|---|---|---|
| Ester | Tensile | Elongation | TXE |
| — | 48 | 24 | 1152 |
| A | 63 | 38 | 2394 |
| B | 57 | 26 | 1482 |
| C | 65 | 39 | 2535 |
| D | 70 | 47 | 3290 |

In each case the esters improved the resistance to aging.

A butadiene/acrylonitrile latex was compounded with three different amine antioxidants alone (2 parts) and in combination (2 parts) with 8 parts of ester D. The latex was coagulated, compounded, vulcanized and aged as the compositions in Table IV. The tensile and elongation results are listed in Table V.

TABLE V

| | | % Retained | | |
|---|---|---|---|---|
| Amine | Ester | Tensile | Elongation | TXE |
| X[1] | — | 35 | 22 | 770 |
| X | D | 64 | 59 | 3776 |
| Y[2] | — | 56 | 43 | 2408 |
| Y | D | 63 | 73 | 4599 |
| Z[3] | — | 26 | 16 | 416 |
| Z | D | 44 | 53 | 2332 |

In each case the ester greatly improved the TXE product.
[1] Polymerized 2,2,4-trimethyl-1,2-dihydroquinoline
[2] Mixture of diaryl paraphenylene diamines
[3] 4,4'-bis(di-alpha-methylbenzyl)-diphenylamine An SBR (butadiene/styrene rubber) containing 0.75 part of a phenolic antioxidant was aged with no additional antioxidant present, with amine antioxidant Z alone (1 part), with ester D alone (1 part) and with Z (0.75 part) and D (0.25 part) in combination.

The aged data (air oven aged 70 hours at 121° C.) are listed in Table VI.

TABLE VI

| | | % Retained | | |
|---|---|---|---|---|
| Z | D | Tensile | Elongation | TXE |
| 1.0 | — | 58 | 35 | 2030 |
| — | 1.0 | 43 | 28 | 1204 |
| 0.75 | 0.25 | 75 | 45 | 3375 |
| — | — | 62 | 35 | 2160 |

As shown above, the combination aged much better than the individual components.

Another SBR polymer containing 0.75 part of amine antioxidant Y was stabilized with additional amounts of other amines alone (1 part) and in combination (0.75 part) with ester D (0.25 part). Aged comparisons were made between vulcanizates so compounded as well as the vulcanizates with ester D alone (1 part) added and no additional stabilizer.

The vulcanizates were aged 70 hours at 121° C. The results are listed in Table VII.

TABLE VII

| | | % Retained | | |
|---|---|---|---|---|
| Amine | Ester | Tensile | Elongation | TXE |
| — | D | 66 | 45 | 2970 |
| Z | — | 72 | 39 | 2808 |
| Z | D | 77 | 53 | 4081 |
| SDPA[4] | — | 65 | 42 | 2730 |
| SDPA | D | 88 | 59 | 5192 |
| NAPMA[5] | — | 51 | 31 | 1581 |
| NAPMA | D | 85 | 55 | 4675 |
| — | — | 58 | 36 | 2090 |

[4] Reaction product of styrene and diphenylamine contains 4,4'-bis(alphamethylbenzyl)-diphenylamine
[5] N-(4-anilinophenyl)methacrylamide The combinations were superior to the individual components even though the total stabilizer system was maintained at the 1.0 part level.

While certain representative embodiments and details have been shown for the purpose of illustrating the invention, it will be apparent to those skilled in this art that various changes and modifications may be made therein without departing from the spirit or scope of the invention.

I claim:

1. 3,6,9-trioxaundecane-1,11-bis(3-n-dodecylthiopropionate).

* * * * *